United States Patent [19]

Iriguchi

[11] 4,424,132
[45] Jan. 3, 1984

[54] APPARATUS AND METHOD FOR SEPARATING BLOOD COMPONENTS

[75] Inventor: Norio Iriguchi, Fuji, Japan

[73] Assignee: Asahi Kasei Kogyo Kabushiki Kaisha, Osaka, Japan

[21] Appl. No.: 344,081

[22] Filed: Jan. 29, 1982

[30] Foreign Application Priority Data

Feb. 5, 1981 [JP] Japan .................................. 56-16190
Sep. 4, 1981 [JP] Japan .................................. 56-140047

[51] Int. Cl.³ ............................................ B01D 21/00
[52] U.S. Cl. .................................... 210/800; 210/804; 210/540; 210/927; 210/745; 422/101
[58] Field of Search ............... 210/800, 801, 803, 804, 210/513, 537, 540, 927, 745, 96.1; 422/101, 102; 435/287

[56] References Cited

U.S. PATENT DOCUMENTS

| | | | |
|---|---|---|---|
| 2,728,457 | 12/1955 | Clarke | 210/521 |
| 3,225,936 | 12/1965 | Ballestra | 210/521 |
| 3,826,740 | 7/1974 | Jewett | 210/927 |
| 3,858,795 | 1/1975 | Joyce | 210/927 |

FOREIGN PATENT DOCUMENTS

| | | | |
|---|---|---|---|
| 453214 | 12/1948 | Canada | 210/801 |
| 1784190 | 7/1979 | Fed. Rep. of Germany | 210/521 |

Primary Examiner—Peter A. Hruskoci
Attorney, Agent, or Firm—Sprung, Horn, Kramer & Woods

[57] ABSTRACT

An apparatus and method for separating blood components by means of sedimentation action due to gravitational force are disclosed. The blood to be separated is continuously passed through a flat blood flow channel having a thickness of 20 mm or less and is separated into multiple streams of the separated blood components. An opening for a feed line of the blood is provided at the upstream side of the blood flow channel and at least two openings for discharge lines of the separated blood components are provided at the downstream side of the blood flow channel.

8 Claims, 6 Drawing Figures

APPARATUS AND METHOD FOR SEPARATING BLOOD COMPONENTS

BACKGROUND OF THE INVENTION

1. Field of the Invention

The present invention relates an improved apparatus and method for separating blood components from blood by means of sedimentation action due to gravitational force.

2. Description of the Prior Art

Blood comprises a plasma component and a blood corpuscle component containing erythrocytes, leucocytes, blood platelets and the like. Recently, hospitals have not been transfusing collected blood whole, but have been frequently separating the collected blood into its components so as to use the specific blood component required by the patient. One method of doing this is to allow the blood to stand, wherein the blood corpuscle components gradually settles to the bottom and separates from the plasma. However, this gravitational method of separation is very slow. For this reason, hospitals have heretofore widely used centrifugal separation for separating blood components rather than gravitational separation. Centrifugal separation, however, is disadvantageous in that it requires an expensive centrifugal separator, which in turn requires high rotational power and safety devices.

SUMMARY OF THE INVENTION

Accordingly, the objects of the present invention are to obviate the above-mentioned disadvantages of the prior arts and to provide an apparatus and method for effectively and efficiently separating blood components, without using artificial centrifugal force, by means of sedimentation action due to gravitational force.

Other objects and advantages of the present invention will be apparent from the description set forth hereinbelow.

In accordance with the present invention, there is provided an apparatus for separating blood components by means of sedimentation action due to gravitational force, comprising:

a sealed vessel;

a blood flow channel comprising a flat empty space having a thickness of 20 mm or less contained inside the sealed vessel;

an opening for a feed line of blood provided at the upstream side of the blood flow channel; and at least two openings for discharge lines of the separated blood components provided at the downstream side of the blood flow channel.

In accordance with the present invention, there is also provided a method for separating blood components by means of sedimentation action due to gravitational force, comprising the steps of:

continuously passing blood to be separated through a blood flow channel, comprising a flat empty space having a thickness of 20 mm or less, while the blood flow channel is filled up;

separating the blood flow into multiple streams of separated blood component layers; and collecting the desired blood component layer or layers.

BRIEF DESCRIPTION OF THE DRAWINGS

The present invention will be better understood from the description set forth below with reference to the accompanying drawings, in which.

DETAILED DESCRIPTION OF THE INVENTION

Figure 1:
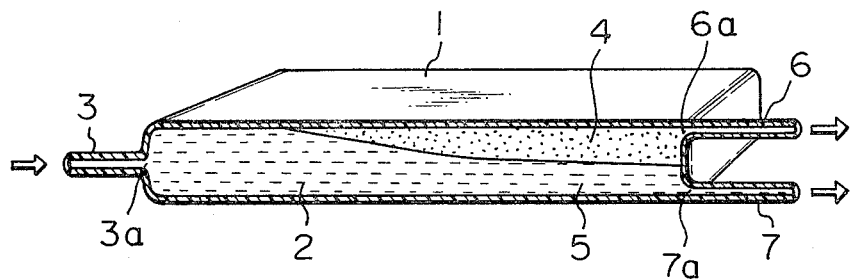
FIG. 1 is a perspective view illustrating one embodiment of the blood component separation apparatus according to the present invention, in which the front is cut so that the inside thereof is clearly understood.

According to the blood component separation apparatus and method of the present invention, the desired blood component or components can be efficiently separated from the blood by just passing the blood through a flat blood flow channel. The separation rate of the present method is larger, by several times, than that of the conventional simple settling method. Furthermore, it is advantageous in that the blood component separation method of the present invention can be carried out by not a batch method but a continuous method.

The reason why the desired blood component or components can be efficiently separated from the blood according to the present invention is not clearly understood, but it would seem as follows. Although blood is a viscous liquid, the factor substantially deciding the viscosity is the ratio of volume of erythrocytes to the whole blood, i.e. a hematocrit value. The hematocrit value of normal human blood is 30 through 45% and the viscosity of the erythrocyte component is 3 through 4 times that of water. When the hematocrit value reaches 60 through 70%, the viscosity of the blood becomes as high as 6 through 9 times that of water. On the other hand, the viscosity of the plasma component in the blood is only 1.5 through 2.0 times that of water, although it depends upon the amount and types of proteins contained in the blood. According to the observation, if blood is once slightly separated into a supernatant layer and a sedimentation layer, when flowing, by erythrocyte sedimentation and other factors, the viscosity of the sedimentation layer is increased. The higher viscosity of the sedimentation layer then creates greater resistance in the sedimentation layer against the external force causing the blood flow. Contrary to this, the lower viscosity of supernatant layer means less resistance against said external force. On the other hand, the viscosity of blood is largely affected by the linear velocity of the blood flow. That is, the lower linear velocity rapidly increases the viscosity of the blood. It appears that this phenomenon is caused by the function of cohesion, especially the adhesion between erythrocyte particles. Actual microscopic observation showed that the erythrocytes tended to form cohesive masses. These cohesive masses are frequently in the form of linked coins. This phenomenon seems to be another factor increasing the resistance of the flow. Furthermore, it is believed that the filled state of the blood flow channel during the blood flow facilitates the formation of the cohesive masses of the erythrocytes and their concentration, because, in addition to the compressing effect of the erythroctye sedimentation (i.e. compressing effect due to downward gravitational force), the sedimentation layer is compressed by the flow (i.e. compressing effect due to lateral external force). It is believed that these phenomena of the blood under a flowing condition effect the blood component separation of the present invention. That is to say, according to the present invention, blood components can be efficiently separated without any moving parts and by just passing blood through the blood flow channel composed of narrow space.

The blood which can be separated by the present invention includes whole blood or a liquid containing, as a main constituent, whole blood and, as a minor constituent, a special blood component, anticoagulant or the like.

The thickness of the blood flow channel of the present invention can be 20 mm or less, practically, 0.2 through 20 mm, and desirably 0.5 through 10 mm. In the case where the depth of the blood flow is more than 20 mm, the sedimentation pass length of the erythrocyte becomes too long, whereby the effective and efficient blood component separation becomes difficult. In the case where the thickness of the blood flow is less than 0.2 mm, the efficiency of the separation of the plasma and the blood corpuscles tends to decrease under practical linear velocity conditions. It is believed that the above-mentioned reduction in separation efficiency is caused by a phenomenon similar to the so-called Fahraeus-Lindqvist effect (that is, when blood flows in capillaries, blood corpuscles do not randomly flow, but are forced to flow in an oriented condition, whereby the viscosity is abnormally decreased).

The linear velocity of the blood flow is desirably 0.5 through 200 mm/min, more desirably 1 through 100 mm/min, and most desirably 2 through 50 mm/min. In the case where the linear velocity of the blood flow is larger than 200 mm/min, effective and efficient blood component separation becomes difficult, as it is likely to cause a turbulent flow and remarkably weaken the cohesion between the erythrocyte particles. On the other hand, in the case where the linear velocity of the blood flow is smaller than 0.5 mm/min, the capacity for treatment of the blood is reduced. Although the length of the blood flow channel can be shortened, in such case, in order to increase the capacity for treatment of the blood, the width of the blood flow channel would have to be increased. Such an increase, however, would likely cause channelling of the blood. The width of the blood flow channel is desirably 50 through 500 mm, more desirably 100 through 300 mm.

The temperature of the blood flow is desirably 35° through 42° C., more desirably 37° through 40° C. The separation efficiency becomes large, as the temperature of the blood to be separated becomes high. However, in the case where the temperature of the blood becomes too high, the hemolysis of the erythrocytes and the denaturation of enzymes might be caused.

The blood flow channel is desirably mounted in such a manner that the blood to be separated flows in the blood flow channel in an upward direction at an angle more than the substantial horizontal plane but less than approximately 45°. The term "substantial horizontal plane" means somewhat ascending and descending plane and includes an inclination within approximately ±10° from the horizontal plane. A downward direction of flow is undesirable as an air layer is likely to remain in the blood flow channel. Contact of the blood with an air layer tends to cause coagulation of the blood during the continuous flow of the blood and the blood flow should be carefully deaerated to remove the air layer. Too great an upward angle of flow is also undesirable, since the higher the angle, the lower the separation efficiency. For easy deaeration and effective space utilization, however, one can set the angle to as much as approximately 45° in practical use, though an angle of 20° or less would be more desirable. Of course, it should be noted that not necessarily all of the blood flow channel has to be upwardly inclined. The inclusion of any descending portion in the channel, however, is not desirable due to the fact that air retaining portions may be formed.

A desirable apparatus for separating blood components according to the present invention comprises a sealed vessel containing a blood flow channel through which the blood to be separated flows on an upward direction at an angle more than substantial horizontal plane but less than approximately 45°. In the blood flow channel, an opening for a feed line of the blood is provided at the upstream side of the blood flow channel and at least two openings for discharge lines of the separated blood components are provided at the downstream side of the blood flow channel.

The reasons that a sealed vessel is used are to enable control of the linear velocity of the blood flow to the desired value, to conrol the thickness of the blood flow to a suitable value and to prevent the contamination of the blood by foreign materials.

The sealed vessel is desirably composed of a bottom surface and a top surface, which are substantially flat. The term "substantially flat" does not necessarily mean a microscopic smoothness. Especially, relatively rough materials can be used as the bottom surface to provide additional resistance against the blood flow. For this reason, a bottom surface having an uneven or irregular surface can be sometimes used in the present invention. Especially, numerous irregular portions having sizes above that of erythrocyte particles can be advantageously used. Furthermore, the surface area of the bottom surface of the blood flow channel can be enlarged by using a corrugated plate having corrugations parallel to the direction of the blood flow. Still further, in order to maintain the thickness of the blood flow channel constant, suitable means, for example, spacers can be mounted in the blood flow channel parallel to the flow direction of the blood so that the thickness of the blood flow channel is kept constant. As mentioned hereinabove, the thickness of the blood flow channel is desirably 20 mm or less.

From a practical point of view, the volume of the apparatus according to the present invention is at least 50 ml. Furthermore, when the apparatus of the present invention is used for the purpose of external circulation of human blood by connecting the apparatus to a human blood vessel, or when separating a one-man portion of collected blood contained in a blood bag the volume of the apparatus is desirably 500 ml or less.

The flow rate of the blood is such that the residence time of the blood in the blood flow channel is desirably 2 through 20 min, more desirably 4 through 15 min, although it may be varied depending upon, for example, the size or the shape of the apparatus. In the case where the residence time is too short, the separation can not be fully effected due to the too large flow rate of the blood. Contrary to this, in the case where the residence time is too long, the volume of the desired separated blood component which can be collected by the appratus is undesirably small. As a general trend, the smaller the thickness of blood flow channel, the greater the amount of the separated blood component obtainable in a short residence time.

The term "residence time T (min.)" used herein is defined by the following equation:

$$T = (S \times D)/Q$$

Wherein
S: area of blood flow channel (cm$^2$)
D: thickness of blood flow channel (cm)
Q: flow rate of blood (cm$^3$/min)

The preferred embodiments of the present invention will now be illustrated in detail in connection with the accompanying drawings.

In FIG. 1, a sealed vessel 1 contains a blood flow channel having a substantially flat bottom plate. The bottom plate is maintained in such a manner that blood to be separated is passed through the blood flow channel 2 in a substantially horizontal direction or upward direction. The blood, usually containing an anticoagulant, is continuously fed through a feed line 3 via an opening 3a to one end of the blood flow channel 2. The blood thus fed is gradually separated along the blood flow channel into a supernatant layer 4 comprising platelet rich plasma and a sedimentation layer 5 comprising blood corpuscles containing erythrocytes and leucocytes. The sedimentation layer 5 is sometimes further separated, whereby a leucocyte layer floating on an erythrocyte layer is formed, as an intermediate layer. The separated components at the downstream side of the blood flow channel 2 are continuously discharged via openings 6a and 7a, which are located in the supernatant layer 4 and the sedimentation layer 5, respectively, through a discharge line 6 and a discharge line 7. In the embodiment shown in FIG. 1, the openings 6a and 7a are provided at the uppermost portion and the lowermost portion of the blood component streams at the end of the downstream side of the blood flow channel 2, respectively. Thus the platelet rich plasma is discharged through the discharge line 6 and the blood corpuscles are discharged through the discharge line 7.

For better effect, one can previously add plasma to the blood to be introduced through the feed line 3. This previous addition of plasma to the blood increases the amount of the platelet rich plasma discharged through the discharge line 6. Experiments have confirmed, however, that even when said previously added plasma contains substantially no platelets, the amount of platelets contained per unit amount of the platelet rich plasma discharged through the discharge line 6 decreases at a smaller rate than said increase in the amount of platelet rich plasma. As a result, the amount of the separated and discharged blood platelets per unit time is increased.

Furthermore, as mentioned hereinabove, the erythrocyte sedimentation effect is essential to the present invention. However, the erythrocyte sedimentation effect is sometimes small for certain types of blood to be separated, especially when the blood is in the state of polycythemia. In this case, the inclusion of plasma in the blood to be fed increases the effect of the present invention.

In addition, in the case of very anemic blood having a hematocrit value of 20% or less, concentrated erythrocytes can be previously added to the blood to be fed or a portion of the blood corpuscles discharged from the discharge line 7 can be previously added to the blood to be fed, to effectively increase the probability of erythrocyte cohesion.

Figure 2:
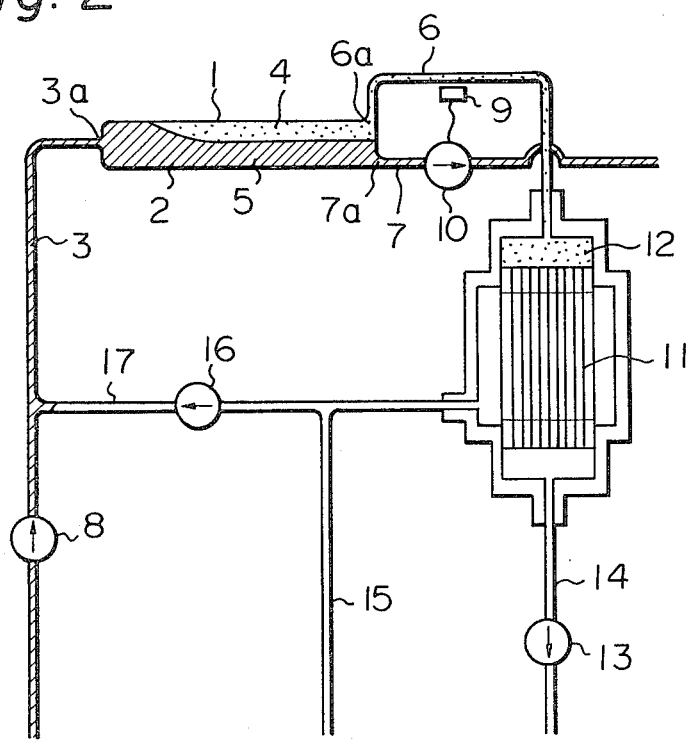
FIG. 2 is a schematic view illustrating one embodiment of the blood component separation system in which the apparatus of FIG. 1 is used.

In FIG. 2, blood to be separated is fed to a blood flow channel 2 in a sealed vessel 1 through a feed line 3 via an opening 3a by means of a pump 8. The blood fed to the blood flow channel 2 is separated into a supernatant layer 4 comprising platelet rich plasma and a sedimentation layer 5 comprising blood corpuscles. The supernatant layer 4 is discharged from a discharge line 6 through an opening 6a, and the sedimentation layer 5 is discharged from a discharge line 7 through an opening 7a.

In order to detect whether or not components of the sedimentation layer are included in the discharged supernatant layer, a detector 9 is installed in the discharge line 6. A pump 10 linked to the detector 9 is installed in the discharge line 7. That is, when the detector 9 detects contamination of the supernatant layer by components of the sedimentation layer, it actuates the pump 10 to initiate the discharge of the sedimentation or to increase the discharge flow rate of the sedimentation layer. As a result, the separation boundary surface between the supernatant layer and the sedimentation layer is downwardly moved. Thereafter, when the detector 9 no longer detects the above-mentioned contamination, the pump 10 is actuated to stop the discharge or to decrease the discharge flow rate. Thus, the separation boundary surface in the blood flow channel is controlled to a predetermined level. As a detector, an optical type detector can be suitably used due to the fact that an optical type detector does not adversely affect the separated components. Generally speaking, an optical type detector is suitable for use in the detection of the contamination of plasma by blood corpuscles rather than detection of the contamination of blood corpuscles by plasma.

The platelet rich plasma discharged through the discharge line 6 is introduced into a filter chamber 12 provided with porous membrane filter 11, wherein platelet poor plasma is filtered and the plasma containing concentrated blood platelet is discharged through a discharge line 14 by means of a pump 13. The filtered platelet poor plasma is discharged through a discharge line 15, and portion thereof is added to the blood to be fed to the blood flow channel through the feed line 3 via a tube 17, by means of a pump 16, for the above-mentioned technical reasons. The porous membrane filter suitably used in the present invention are those which have an approximately uniform pore size of a maximum 2 microns or less. In the case where the maximum pore size of the membrane filter is less than 0.1 micron, not only the blood platelets contained in the platelet rich plasma are concentrated, but also the protein component tends to be concentrated and, further, the concentration rate is undesirably reduced. On the other hand, in the case where the maximum pore size of the membrane filter is greater than 2 microns, the blood platelets having a relatively small size tends to be filtered. The desirable pore size is 0.1 through 1 micron, more desirably 0.1 through 0.5 micron. The maximum pore size greater than 1 micron tends to result in adherence and build-up of platelets on the surface of the porous membrane filter, thereby clogging the membrane filter. However, in the case where the maximum pore size of the membrane filter is 1 micron or less, not only the filtration of the blood platelet through the membrane filter is stopped, but also the built-up or clogging of the blood platelet on the surface of the membrane is effectively prevented. As a result, the concentrated blood platelets can be readily obtained.

Porous membrane filter made of polyethylene, polypropylene, cellulose acetate, polycarbonate, polyvinylidene fluoride and the like is desirably used in the present invention. For effective filtration, the pressure difference of the membrane filter is practically 1 through 500 mmHg, desirably 5 through 100 mmHg. Although the porous membrane filter can be a flat membrane, a membrane in the form of hollow fibers is desirably used in the present invention due to its relatively compact construction.

The flow rate of the platelet rich plasma to be fed to the filter chamber can be widely determined depending upon, for example, the opening space ratio of the membrane filter, the filtering pressure, and the area of the membrane. For instance, a flow rate of 4 through 40 ml/min can be practically used. The flow rate of the platelet concentrated plasma discharged through the discharge line 14 can be practically 1/20 through $\frac{1}{2}$ of the flow rate of the platelet rich plasma introduced into the filter chamber 12. In the case where the flow rate is less than 1/20, the blood platelets tend to adhere onto the surface of the porous membrane filter, whereby the membrane filter is clogged and the blood platelets build up on the surface of the membrane filter. Contrary to this, in the case where the flow rate ratio is greater than $\frac{1}{2}$, the desired concentration of the plasma cannot be achieved.

Figure 3:
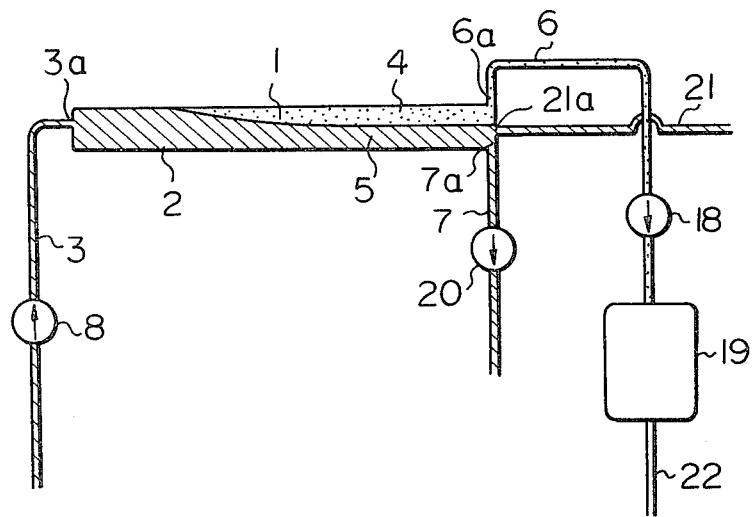
FIG. 3 is a schematic view illustrating one embodiment of the blood component separation system using a modified apparatus of the apparatus shown in FIG. 1.

In FIG. 3, the supernatant layer 4 separated in the blood flow channel 2 is discharged from a discharge line 6 and introduced into a column 19 by means of a pump 18. On the other hand, the sedimentation layer 5 separated in the blood flow channel 2 is discharged through a discharge line 7 by means of a pump 20 to the outside of the system. In the sealed vessel 1, in addition to openings 6a and 7a for discharge lines 6 and 7, respectively, another opening 21a is provided at an intermediate height between the openings 6a and 7a and is connected to a discharge line 21. In the case where the separation boundary surface of the supernatant layer and the sedimentation layer moves up from the level of the opening 21a, the component of the sedimentation layer 5 can be discharged through opening 21a. On the other hand, when said boundary surface moves down from the level of the opening 21a, the component of the supernatant layer 4 can be discharged through the opening 21a. Thus, the level of said separation boundary surface can be controlled to a desired level and the contamination of the platelet rich plasma dishcarged through the discharge line 6 by the component of the sedimentation layer can be eliminated. When the separation further proceeds, a leucocyte layer sometimes floats on the erythrocyte layer as an intermediate layer. This intermediate layer can also be discharged through the discharge line 21 to the outside of the system.

The column 19 is packed with an adsorbing substance, for example, acrylic fibers. The blood platelets floating in the platelet rich plasma and the leucocytes contained therein are adsorbed by the adsorbing substance and removed from the plasma and, therefore, platelet poor plasma can be discharged through a discharge line 22. As the adsorbing substances, in addition to the acrylic fibers, various natural or synthetic fibers such as polyester, nylon, rayon, cotton, and silk can be used in the present invention. Although there is no critical limitation on the denier of these fibers, practically fibers having a denier of 0.1 through 5 can be used. Futhermore, the column can be practically packed with these fibers at a packing density of 0.05 through 0.5 g/ml and the volume of the column 19 can be practically 10 through 100 ml, in the case where 500 ml of the platelet rich plasma is treated.

A column in which an activated carbon, an ion exchange resin, alumina or the like is packed, or an affinity column in which an antigen-antibody reaction is carried out can also be used for column 19 in the present invention, whereby a soluble toxic substance contained in the plasma can be removed.

Figure 4:
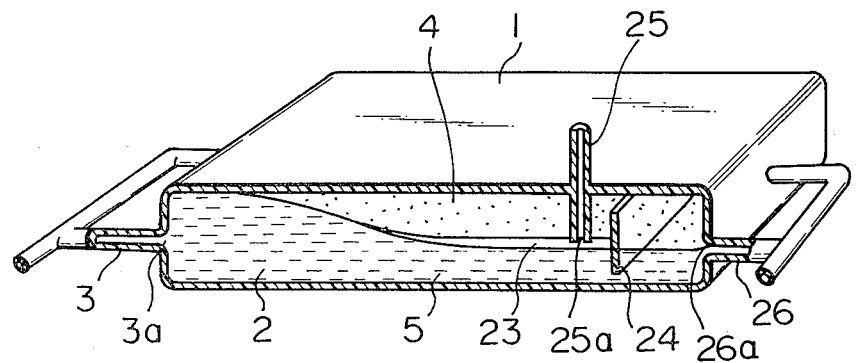
FIG. 4 is a perspective view illustrating another embodiment of the blood component separation apparatus according to the present invention, in which the front is cut so that the inside thereof is clearly understood.

In FIG. 4, a weir 24 is mounted at the downstream side of the blood flow channel 2 of the sealed vessel 1 in such a manner that only the flow of the intermediate layer containing a large amount of leucocytes can be blocked. In order to discharge the blocked intermediate layer 23, an opening 25a is provided at the upstream side of the weir 24. An opening 26a is provided at the downstream side of the weir 24 in such a manner that it is somewhat lower in level than that of the opening for a discharge line 25. The supernatant layer 4 flows over the weir 24, and is discharged with the sedimentation layer 5 through a discharge line 26. However, in the case where the separation boundary surface between the supernatant layer 4 and the sedimentation layer 5 moves up from the level of the opening 26a, the component contained in the sedimentation layer is discharged through the opening 26a. On the other hand, when the separation boundary surface moves downward from the level of the opening 26a, the component contained in the supernatant layer is discharged through the opening 26a. This allows the level of the separation boundary surface to be controlled, whereby the level of the intermediate layer 23 which is located approximately on the separation boundary surface is controlled. In FIG. 4, it should be noted that a further discharge line for discharging the supernatant layer comprising platelet rich plasma can be provided in the sealed vessel 1. Furthermore, in order to discharge the sedimentation layer 5 comprising erythrocytes, a still further discharge line can be provided, or the above-mentioned two further discharge lines can be provided in the sealed vessel 1 instead of the discharge line 26. In fact, the component of the sedimentation layer 5 is often included in the intermediate layer discharged through the discharge line 25. Accordingly, the intermediate layer 23 discharged through the discharge line 25 is introduced into another apparatus of the present invention, wherein the component of the sedimentation layer 5 can be sedimented and removed.

Figure 5:
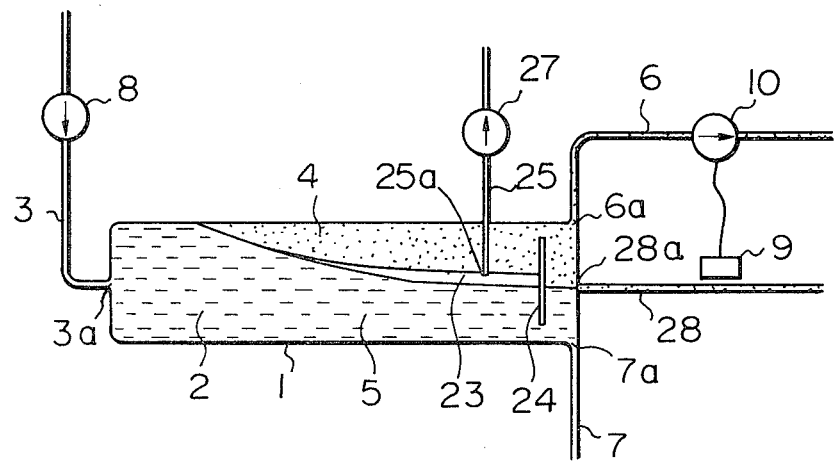
FIG. 5 is a schematic view illustrating one embodiment of the blood component separation system in which the apparatus shown in FIG. 4 is used.

In FIG. 5, a pump 27 is mounted on the discharge line 25. An opening 28a of a discharge line 28 is provided at the downstream side of the weir 24 and at a level approximately the same as that of the opening 25a of the discharge line 25. In the discharge line 28, a detector 9 is provided for detecting the concentration of the supernatant layer 4 or sedimenation layer 5 discharged from the opening 28a. A pump 10 linked with the detector 9 is mounted in a discharge line 6. When the detector 9 detects the presence of the component of the sedimentation layer 5, it actuates the pump 10 to decrease the discharge flow rate therethrough or stops the pump 10. As a result, the separation boundary surface between the supernatant layer 4 and the sedimentation layer 5 moves downward. When the detector 9 no longer detects the above-mentioned component and, then, the pump 10 is actuated in such a manner that the discharge flow rate therethrough is increased or the pump 10 is started. When the weir 24 and the discharge line 25 are not mounted, the intermediate layer 23 is discharged through the discharge line 28. In this case, the detector 9 detects whether or not the intermediate layer 23 is contaminated with other components.

The sealed vessel used in the present invention should be made of rigid materials which will not deform by inside pressure. Furthermore, the sealed vessel should be made of nontoxic and antithrombosis materials. However, it is also possible to make the sealed vessel from nonrigid thin materials, followed by being supported with a rigid material. The materials which can be used in the manufacture of the sealed vessel include rigid materials such as polycarbonate resin, rigid polyvinyl chloride resin, acrylic resin and aluminum; and nonrigid materials such as silicone resin, nonrigid polyvinyl chloride resin and polyethylene resin.

Figure 6:
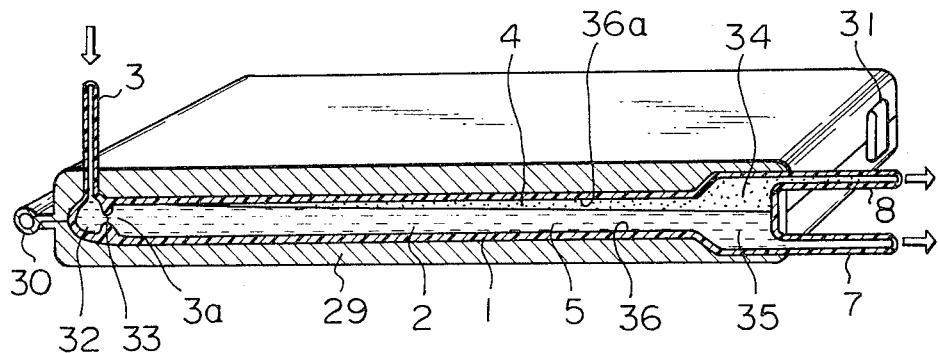
FIG. 6 is a perspective view illustrating a further embodiment of the blood component separation apparatus according to the present invention in which the front is cut so that the inside thereof is clearly understood.

FIG. 6 is a perspective view illustrating a practical embodiment of the blood-component separation apparatus of the present invention, in which a nonrigid sealed vessel is supported by a stiff material. That is, the vessel in FIG. 6 is made of silicone resin and, in order not to deform by the inside pressure, the silicone resin vessel is substantially supported in a shell 29 made of aluminum. The shell 29 has a high heat transfer coefficient and, therefore, is suitable for maintaining the appropriate temperature of the blood contained in the vessel 1. Of course, in order to heat the shell 29, an appropriate heater can be embedded therewithin. The shell 29 can be opened and closed by means of a hinge 30 and can be locked by a means 31. In the vessel 1, a blood pool 32 and a slit 33 are provided between the feed line 3 and the opening 3a, to prevent channelling of the blood. Furthermore, a supernatant layer pool 34 and a sedimentation layer pool 35 are also provided at the downstream side of the blood flow channel 2. In order to ensure a predetermined distance between the bottom surface 36 and the top surface 36a of the blood flow channel 2 contained and sealed in the vessel 1, a spacer or spacers can be provided in the vessel 1 in such a manner that the blood flow is not adversery affected. The spacers can be plural protrusions attached to at least one surface of the bottom surface 36 and top surface 36a.

Since blood component separation vessels are usually made disposable from a sanitary point of view, the embodiment as shown in FIG. 6 is advantageous.

It is also possible that a plurality of sealed vessels be used in such a way that the blood to be separated is fed individually into the blood flow channel of each vessel for independent separation of the blood components, then the independently separated portions of each type of blood components be combined and discharged all together. This is effective in that it decreases the linear velocity, especially when the thickness of the blood flow channel is small, and also prevents channelling of the blood flow. Mounting of said sealed vessels in multiple layers would also allow a more compact blood component separation apparatus. Another compact design of the sealed vessel could be a single sealed blood flow channel formed as a multi-layer spiral of a small pitch, said pitch providing an inclination to the bottom surface of the blood flow channel. So long as said pitch is not too large, it would provide the inclination for a gentle upward or downward flow of the blood.

As mentioned hereinabove, according to the present invention, blood components can be separated by using very simple step and means, without applying centrifugal force to the blood.

The invention has been described in detail with particular reference to certain preferred embodiments thereof, but it will be understood that variations and modifications can be effected by those skilled in the art within the spirit and scope of the invention.

EXAMPLES

The present invention will now be further illustrated by, but is by no means limited to, the following examples.

EXAMPLE 1

Blood component separation apparatuses as shown in FIG. 1 were made using acrylic resin. The dimensions are shown in Table 1 below. Blood component separation experiments were carried out using these apparatuses in a system as shown in FIG. 2, except that the filtering device was omitted. Porcine blood, having an erythrocyte sedimentation rate of 56 mm (1 hr) at 37° C. and to which heparin was added to prevent the coagulation, was heated to a temperature of 37° C. and fed to the blood flow channel through a blood feed line at a flow rate of 10 ml/min by means of a pump 8. Thus, the blood components were separated. The separation operation was carried out in such a manner that the concentrated erythrocytes forming the sedimentation layer were pumped out while keeping the erythrocyte concentration in the platelet rich plasma approximately constant by means of a detector 9 controlling a pump 10. The platelet rich plasma was obtained from the discharge line 6. The flow rate and the separation efficiency (amount of plasma/amount of whole blood) (%) of the platelet rich plasma thus obtained are shown in Table 1 below.

TABLE 1

| Exp. No. | Blood Flow Channel Vol. (cm$^3$) | Thickness (mm) | Linear Velocity of Blood (cm/min) | Residence Time (min) | Flow Rate of Platelet Rich Plasma (ml/min) | Separation Efficiency (%) |
|---|---|---|---|---|---|---|
| 1 | 52 | 1 | 5.0 | 5.2 | 3.8 | 38 |
| 2 | 52 | 2 | 5.0 | 5.2 | 3.2 | 32 |
| 3 | 65 | 5 | 2.0 | 6.5 | 2.3 | 23 |
| 4 | 195 | 15 | 0.67 | 19.5 | 1.6 | 16 |

EXAMPLE 2

Blood component separation apparatuses having the same thickness as that of No. 2 of Example 1 were manufactured. Blood separation experiments were carried out using these apparatuses in the same flow rate of blood as described in Example 1. The erythrocyte sedimentation rate of the porcine blood used was 46 mm at 37° C. The volumes of a blood flow channel of the apparatuses and the results of the separation experiments are shown in Table 2 below.

TABLE 2

| Exp. No. | Blood Flow Channel Vol. (cm³) | Residence Time (min) | Flow Rate of Platelet Rich Plasma (ml/min) | Separation Efficiency (%) |
|---|---|---|---|---|
| 1 | 40 | 4.0 | 1.3 | 13 |
| 2 | 80 | 8.0 | 2.7 | 27 |
| 3 | 120 | 12.0 | 3.5 | 35 |

EXAMPLE 3

A blood component separation apparatus having the same dimensions as that of experiment No. 2 of Example 1 was manufactured. Blood component separation experiments were carried out in the same manner as described in Example 1, except that the flow rate of the blood was changed and the erythrocyte sedimentation rate of the porcine blood used was 49 mm at 37° C. The results obtained from the experiments in which the flow rates of the blood were changed are shown in Table 3 below.

TABLE 3

| Exp. No. | Flow Rate of Blood (ml/min) | Residence Time (min) | Flow Rate of Platelet Rich Plasma (ml/min) | Separation Efficiency (%) |
|---|---|---|---|---|
| 1 | 12 | 4.3 | 1.8 | 15 |
| 2 | 7.5 | 6.9 | 1.9 | 25 |
| 3 | 3.5 | 14.9 | 1.3 | 37 |

EXAMPLE 4

A blood component separation apparatus as shown in FIG. 1 having a volume of a blood flow channel of 300 cm³ and a thickness of the blood flow channel of 2 mm was manufactured using acrylic resin. Blood separation experiments were carried out in the same manner as described in Example 1, except that the flow rates of the blood were changed and the erythrocyte sedimentation rate of the porcine blood was 81 mm at 37° C. The results obtained from the separation experiments are shown in Table 4 below. As Comparative Examples, the separation results obtained from comparative experiments in which blood was allowed to stand in the same vessel are also shown in Table 4 below. In Table 4, experiment Nos. 1 through 5 are working examples and experiments Nos. 6 through 10 are comparative examples.

TABLE 4

| Exp. No. | Method | Flow Rate of Blood (ml/min) | Residence Time (min) | Flow Rate of Platelet Rich Plasma | Separation Efficiency (%) |
|---|---|---|---|---|---|
| 1 | Present Invention | 100 | 3 | 14.1 ml/min | 14 |
| 2 | Present Invention | 60 | 5 | 19.9 ml/min | 33 |
| 3 | Present Invention | 20 | 15 | 8.0 ml/min | 40 |
| 4 | Present Invention | 10 | 30 | 4.6 ml/min | 46 |
| 5 | Present Invention | 5 | 60 | 2.5 ml/min | 50 |
| 6 | Settling | (300) | 2 | ~0 (ml/hr) | 0 |
| 7 | Settling | (300) | 5 | 10 (ml/hr) | 0 |

TABLE 4-continued

| Exp. No. | Method | Flow Rate of Blood (ml/min) | Residence Time (min) | Flow Rate of Platelet Rich Plasma | Separation Efficiency (%) |
|---|---|---|---|---|---|
| 8 | Settling | (300) | 15 | 25 (ml/hr) | 8 |
| 9 | Settling | (300) | 30 | 65 (ml/hr) | 22 |
| 10 | Settling | (300) | 60 | 80 (ml/hr) | 27 |

EXAMPLE 5

A blood separation apparatus as shown in FIG. 1 was manufactured using acrylic resin. The volume of the blood flow channel was 26 ml and the thickness of the blood flow was 2 mm. Porcine blood having an erythrocyte sedimentation rate of 65 mm at 37° C. and to which heparin was added as an anticoagulant was fed through a blood feed line 3 via an opening 3a at a flow rate of 5.4 ml/min. The linear velocity of the blood flow was 27 mm/min.

While the temperature of the experimental system was kept at 37° C., blood separation experiments were carried out by changing the degree of inclination of the blood flow channel. The flow rate of the platelet rich plasma discharged through the discharge opening 6a and the separation efficiency are shown in Table 5 below.

TABLE 5

| Inclination (degree) | Flow Rate of Plasma (ml/min) | Separation Efficiency (%) |
|---|---|---|
| −12 | 0 | 0 |
| −8 | 0.43 | 8.0 |
| 0 | 1.81 | 33 |
| 11 | 1.57 | 29 |
| 15 | 1.34 | 25 |
| 21 | 1.10 | 20 |
| 29 | 0.90 | 17 |
| 45 | 0.45 | 8.3 |
| 60 | 0.09 | 1.7 |

I claim:

1. An apparatus for separating blood components by means of sedimentation action due to gravitational force, comprising:
   a sealed vessel;
   a horizontally arranged blood flow channel comprising a flat empty space of 50 to 500 ml contained inside the sealed vessel, the space having a thickness of 0.2 to 20 mm and a width of 50 to 500 mm for separating said blood components into a supernatent layer comprising platelet rich plasma, and a sedimentation layer comprising blood corpuscles containing erthrocytes and leucocytes;
   an opening for feeding blood horizontally into the upstream side of the blood flow channel; and
   at least two openings for discharge lines of the separate blood components provided at the downstream side of the blood flow channel, one of said openings located at the uppermost portion of said downstream side for discharging said supernatent layer, and another of said openings located at the lowermost portion of said downstream side for discharging said sedimentation layer.

2. An apparatus as claimed in claim 1, wherein a third opening is located at an intermediate position in the downstream side of the blood flow channel.

3. An apparatus as claimed in claim 1, wherein a weir is mounted at an intermediate height at the downstream side in such a manner that the weir blocks a portion of the blood flow, and wherein one opening for the discharge line is located at an intermediate height at the upstream side of the weir and said at least two other openings for the discharge lines are located at an upper height and a lower height at the downstream side of the weir.

4. A method for separating blood components by means of sedimentation action due to gravitational force, comprising the steps of:

continuously passing blood to be separated at a temperature of 35° to 42° C. horizontally through a blood flow channel comprising a flat empty space of 50 to 500 ml, the space having a thickness of 0.2 to 20 mm and a width of 50 to 500 mm, while the blood flow channel is filled up, the residence time of the blood flow in the blood flow channel being within the range of 2 through 20 minutes; separating the blood flow into a supernatent layer comprising platelet rich plasma, and a sedimentation layer comprising blood corpuscles containing erythrocytes and leucocytes, and removing said supernatent layer and said sedimentation layer from the downstream side of said blood flow channel.

5. A method as claimed in claim 4, wherein the blood flow is passed through the blood flow channel in an upward direction at an angle more than the substantial horizontal plane but less than approximately 45°.

6. A method as claimed in claim 4, wherein the level of the at least one separation boundary surface of the multiple streams is controlled to a predetermined height by the adjustment of the discharge rate of the separated blood streams, whereby the blood components are separated.

7. A method as claimed in claim 4, wherein blood diluted with plasma is passed through the blood flow channel.

8. A method as claimed in claim 4, wherein a weir is mounted at an intermediate height at the downstream side in such a manner that the weir blocks a portion of the blood flow, whereby a portion of the separated blood component in the form of a layer is collected from the upstream side of the weir.

* * * * *